United States Patent
Ligneau et al.

(12)

(10) Patent No.: US 12,059,416 B2
(45) Date of Patent: Aug. 13, 2024

(54) COMBINATIONS OF A H3 ANTAGONIST AND A NORADRENALINE REUPTAKE INHIBITOR, AND THE THERAPEUTICAL USES THEREOF

(71) Applicant: BIOPROJET, Paris (FR)

(72) Inventors: Xavier Ligneau, Saint-Grégoire (FR); Laurent Landais, Ercé-Près-Liffré (FR); David Perrin, Gévezé (FR); Jeanne Marie Lecomte, Paris (FR); Jean Charles Schwartz, Paris (FR)

(73) Assignee: BIOPROJET, Paris (FR)

( * ) Notice: Subject to any disclaimer, the term of this patent is extended or adjusted under 35 U.S.C. 154(b) by 108 days.

(21) Appl. No.: 17/456,617

(22) Filed: Nov. 26, 2021

(65) Prior Publication Data

US 2022/0079932 A1    Mar. 17, 2022

Related U.S. Application Data

(62) Division of application No. 16/431,063, filed on Jun. 4, 2019, now Pat. No. 11,229,632.

(30) Foreign Application Priority Data

Jul. 27, 2018    (EP) .................................... 18306017

(51) Int. Cl.
| | |
|---|---|
| *A61K 31/4545* | (2006.01) |
| *A61K 31/381* | (2006.01) |
| *A61K 31/4453* | (2006.01) |
| *A61P 25/26* | (2006.01) |

(52) U.S. Cl.
CPC ........ *A61K 31/4545* (2013.01); *A61K 31/381* (2013.01); *A61K 31/4453* (2013.01); *A61P 25/26* (2018.01)

(58) Field of Classification Search
CPC ................................................ A61K 31/4545
See application file for complete search history.

(56) References Cited

U.S. PATENT DOCUMENTS 8,076,329 B2    12/2011    Bertrand et al.

FOREIGN PATENT DOCUMENTS

| EP | 1717234 A1 | 11/2006 |
|---|---|---|
| EP | 3239138 A1 | 11/2017 |
| WO | 0006254 A2 | 2/2000 |
| WO | 2006/117609 A2 | 11/2006 |
| WO | 2006117611 A1 | 11/2006 |
| WO | 2018172344 A1 | 9/2018 |
| WO | 2018172432 A1 | 9/2018 |

OTHER PUBLICATIONS

Guo et al., "Differential effects of acute and repeat dosing with the H3 antagonist GSK189254 on the sleep-wake cycle and narcoleptic episodes in Ox−/− mice", British Journal of Pharmacology, 2009, pp. 104-111, vol. 157.
Bymaster et al., "Atomoxetine Increases Extracellular Levels of Norepinephrine and Dopamine in Prefrontal Cortex of Rat: A Potential Mechanism for Efficacy in Attention Deficit/Hyperactivity Disorder", Neuropsychopharmacology, 2002, pp. 699-711, vol. 27, No. 5.
EP Search Report, dated Jan. 29, 2019, from corresponding FR Application No. 18306017.
Kallweit et al., "Pharmacological management of narcolepsy with and without cataplexy", Expert Opinion on Pharmacotherapy, 2017, pp. 809-817, vol. 18, No. 8.
Lin et al., "An inverse agonist of the histamine H3 receptor improves wakefulness in narcolepsy: Studies in orexin −/− mice and patients", Neurobiology of Disease, 2008, pp. 74-83, vol. 30.
Sullivan et al., "Emerging drugs for common conditions of sleepiness: obstructive sleep apnea and narcolepsy", Expert Opinion on Emerging Drugs, 2015, pp. 571-582, vol. 20, No. 4.
Brabant et al., "The histamine H3-receptor inverse agonist Pitolisant improves fear memory in mice", Behavioural Brain Research, 2013, pp. 199-204, vol. 243.
Bymaster et al., "The Dual Transported Inhibitor Duloxetine: A Review of its Preclinical Pharmacology, Pharmacokinetic Profile, and Clinical Results in Depression," Current Pharmaceutical Design, 2005, 11, 1475-1493.
Flik et al., "Interaction Between Brain Histamine and Serotonin, Norepinephrine, and Dopamine Systems: In Vivo Microdialysis and Electrophysiology Study," J. Mol. Neurosci. 2015.
Kleinlogel, "Analysis of the Vigilance Stages in the Rat by Fast Fourier Transformation," Neuropsychobiology, 1990-91:23:197-204.
Igneau et al., "BF2.649 [1-{3-[3-(4-Chlorophenyl)propoxy]propyl}piperidine,Hydrochloride], a Nonimidazole Inverse Agonist/Antagonist at the Human Histamine H3 Receptor: Preclinical Pharmacology," The Journal of Pharmacology and Experimental Therapeutics, vol. 320, No. 1, 2007.
Louis et al., "Design and validation of a computer-based sleeping-scoring algorithm," Journal of Neuroscience Methods 133(2004) 71-80.
Medhurst et al., "GSK189254, a Novel H3 Receptor Antagonist That Binds to Histamine H3 Receptors in Alzheimer's Disease Brain and Improves Cognitive Performance in Preclinical Models," The Journal of Pharmacology and Experimental Therapeutics, vol. 321, No. 3, 2007.
Sanchez et al., "Depression and poor sleep: The effect of monoaminergic antidepressants in a pre-clinical model in rats," Pharmacology, Biochemistry and Behavior 86 (2007) 468-476.
Barbier et al., "Pharmacological characterization of JNJ-28583867, a histamine H3 receptor antagonist and serotonin reuptake inhibitor", European Journal of Pharmacology, vol. 576, 2007, pp. 43-54.
Belikov, "Pharmaceutical Chemistry", Moscow, Vysshaya shkola, 1993, pp. 43-47.
Duloxetinum, Drug reference book GEOTAR "duloxetine". List of data[on-line] Jul. 23, 2017 [found on Dec. 21, 2022]—found on the Internet: URL:https://web.archive.org/web/20170723230915/https://www.Isgeotar.ru/duloxetin.html), pp. 1-13.

(Continued)

*Primary Examiner* — Yong S. Chong
(74) *Attorney, Agent, or Firm* — NIXON & VANDERHYE (57) ABSTRACT

Disclosed are combinations of a H3 antagonist and an antidepressant, which exhibit a synergistic wake promoting activity.

5 Claims, 5 Drawing Sheets

(56) References Cited

OTHER PUBLICATIONS

Gruzner, Nursing and Treatment of Alzheimer's Disease, Xinhua Press, Jan. 2003, pp. 1-3.
Kharkevich, Pharmacology: Manual—9 th edition, revised, corrected and amended—Moscow: GEOTAR—Media, 2006, pp. 1-758.
Shiyin et al., Alcohol-induced Psychoneurological Diseases, Tianjin Science and Technology Press, Nov. 2011, pp. 1-4.
Vengerovsky, A.I. Pharmacological incompatibility / Bulleten SibirskoyMeditsiny (Bulletin of Siberian Medicine), 2003, 3, pp. 49-56.
Yuanxun et al., Chinese Molecular Neurology, Anhui Science and Technology Press, Aug. 2015, pp. 1-4.

COMBINATIONS OF A H3 ANTAGONIST AND A NORADRENALINE REUPTAKE INHIBITOR, AND THE THERAPEUTICAL USES THEREOF

CROSS-REFERENCE TO RELATED APPLICATIONS

This patent application is a divisional of U.S. patent application Ser. No. 16/431,063 filed on Jun. 4, 2019, which claims priority to European application No. 18306017.7 filed on Jul. 27, 2018. Each of these applications is incorporated by reference herein in its entirety.

BACKGROUND OF THE INVENTION

Field of the Invention

The present invention concerns novel combinations and their uses for treating wakefulness disorders in patients suffering from deficient noradrenaline release.

Description of the Related Art

Wakefulness is controlled by several monoaminergic neuronal systems in brain, mainly the histaminergic and noradrenergic systems which are active during wake and silent during sleep. Hence, increase in histamine or noradrenaline release results in wake promotion at the expense of sleep states.

Histamine H3 receptor antagonist/inverse agonists (X. Ligneau et al. J. Pharmacol. Exp Ther. 2007, 320, 365, J. S. Lin et al. Neurobiology of Disease 2008, 30, 74, R X Guo et al. Brit. J. Pharmacol. 2009, 157, 104) are known to modulate sleep/wake increasing wakefulness.

WO 2006/117609 discloses H3 ligands such as (3S)-4-{4-[3-(3-methylpiperidin-1-yl)propoxy]phenyl}pyridine 1-oxide of formula:

(A)

herein referred as "compound (A)", and their pharmaceutically acceptable salts, hydrates, or hydrated salts.

Pitolisant (Wakix®) (ie) the monohydrochloride salt of 1-{3-[3-(4-chlorophenyl)propoxy]propyl}piperidine has been one of the first H3 antagonists/inverse agonists on the market and is currently authorized in Europe for the treatment of narcolepsy with or without cataplexy.

The effect of H3 antagonists on noradrenaline has been disclosed in AD Medhurst et al. (J. Pharmacol. Exp. Ther. 2007, 321, 1032-1045), G. Flik et al. (J. Mol. Neurosci. 2015, 56, 320-328) and J. S. Lin et al. (Neurobiology of Disease 2008, 30, 74-83).

Antidepressants with noradrenaline reuptake inhibitor properties such as duloxetine, reboxetine, atomoxetine, venlafaxine . . . (C. Sanchez et al. Pharmacol. Biochem. Behay. 2007, 86, 468) increase wake at the expense of deep sleep and/or REM sleep.

Kallweit ET AL (EXPERT OPINION ON PHARMACOTHERAPY vol. 18, no. 8, 2017, pages 809-817) reports the pharmacological management of narcolepsy with depression, and suggests e.g. venlafaxine.

Lin ET AL (Neurobiology of Disease, vol. 30, no. 1, 2008, pages 74-83) discloses the use of tiprolisant combined with modafinil.

SUMMARY OF THE INVENTION

It has now been discovered that the combination of a H3 antagonist with an antidepressant chosen from the noradrenaline reuptake inhibitors, unexpectedly leads to tremendous increase in the quiet wake and decrease in the REM sleep, which are respectively enhanced/diminished in a supra-additive, synergistic manner as compared to the effect of each compound given alone.

According to a first object, the present invention thus concerns a combination of:

a H3 antagonist or inverse agonist of formula:

(I)

Where in formula (I):
$R^1$ is H or Methyl,
$R^2$ is Cl or where * represents the position of attachment to the phenyl ring,
n is 0 or 1,
and
an antidepressant chosen from the noradrenaline reuptake inhibitors.

According to an embodiment, said H3 antagonist/inverse agonist is chosen from one of the following compounds:

And any of their pharmaceutically acceptable salts, or solvates thereof.

More particularly, said H3 antagonist/inverse agonist is the hydrochloride salt of More particularly said H3 antagonist/inverse agonist is the dihydrochloride, tetrahydrate of

(herein called BP1.3656B)

According to an embodiment, the compounds may be in the form of their free base, or alternatively, in the form of pharmaceutically acceptable salts such as hydrochloride, oxalate, dihydrochloride, hydrobromide, dihydrobromide, naphthalene-1,5-disulfonate, sulfate, ethane-1,2-disulfonate, cyclamate, toluenesulfonate, paratoluenesulfonate, thiocyanate, nitrate, methanesulfonate, dodecylsulfate, naphthalene-2-sulfonate, benzenesulfonate, dichloroacetate, glycerophosphate, 2-hydroxyethanesulfonate, aspartate, maleate, phosphate, ethanesulfonate, camphor-10-sulfonate, glutamate, alginate, pamoate, 2-oxo-glutarate, 1-hydroxy-2-naphthoate, malonate, gentisate, salicylate, tartrate, fumarate, galactarate, citrate, glucuronate, lactobionate, 4-aminosalicylate, glycolate, sesquiglycolate, glucoheptonate, pyroglutamate, mandelate, malate, hippurate, formate, gluconate, lactate, oleate, ascorbate, benzoate, succinate, 4-acetamidobenzoate, glutarate, cinnamate, adipate, sebacate, camphorate, acetate, caproate, nicotinate, isobutyrate, propionate, caprate caprylate, caproate, laurate, palmitate, stearate, undecen-10-oate, caprylate, orotate, carbonate, 5-sulfocalicylate, 1-hydroxy-2-naphtoate, 3-hydroxy-2-naphtoate; and/or solvates such as hydrates, ethanolate, hemiethanolate.

Accordingly, the expression "compound" as used herein also refers to the pharmaceutically acceptable salts thereof and/or the solvates of said unless specified otherwise.

According to an embodiment, the antidepressant is chosen from duloxetine, reboxetine, atomoxetine, desipramine, venlafaxine, desvenlafaxine, more particularly duloxetine. According to an embodiment, said antidepressant is not venlafaxine. According to an embodiment, said antidepressant is a noradrenaline reuptake inhibitor chosen from duloxetine, reboxetine, atomoxetine, desipramine, desvenlafaxine, in particular duloxetine, reboxetine, atomoxetine, desipramine.

According to an embodiment,
said H3 antagonist/inverse agonist is chosen from one of the following compounds:

and any of their pharmaceutically acceptable salts, or solvates; and
said noradrenaline reuptake inhibitor is chosen from duloxetine, reboxetine, and atomoxetine.

According to an embodiment, the combination is the combination of

HCl (pitolisant) with duloxetine

According to another object, the present invention also concerns a pharmaceutical composition comprising a combination according to the invention, wherein both ingredients are administered simultaneously, separately, or staggered over time.

According to another object, the present invention also concerns the combination of the invention for use for treating and/or preventing a disorder chosen from excessive daytime sleepiness, substance such as alcohol abuse disorders, and/or with attention and cognitive deficit, in a patient suffering from deficient noradrenaline release.

The identification of those subjects who are in need of treatment of herein-described diseases and conditions is well within the ability and knowledge of one skilled in the art. A clinician skilled in the art can readily identify, by the use of clinical tests, physical examination, genetic tests and medical/family history, those subjects who are in need of such treatment.

According to an embodiment, said disorder is excessive daytime sleepiness and occurs in a patient suffering from:
Narcolepsy with and without cataplexy,
Idiopathic hypersomnia,
Daytime sleepiness disorders,
Obstructive sleep apnea,
Circadian rhythm sleep-wake disorders,
Parkinson's disease, or
Prader-Willi Syndrome.

According to an alternative embodiment, said disorder is attention and cognitive deficit and occurs in a patient suffering from attention deficit and hyperactivity disorder (ADHD).

According to a further alternative embodiment, said disorder is excessive daytime sleepiness, attention and cognitive deficit and occurs in a patient suffering from depression.

According to a still further alternative embodiment, said disorder is chosen from substance abuse withdrawal syndromes.

It should be noted that the alternative embodiment are not mutually exclusive and may be considered in addition to each other.

Actual dosage levels of the compounds may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors, e.g. the condition of the patient.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of the compounds which is required to achieve the desired biological effect will vary depending upon a number of factors, including the type of formulation of the drug to be administered, the type of disease, the disease state of the patient and the route of administration.

In general terms, the preferred dosage of a drug to be administered is likely to depend on such variables as the type and extent of progression of the disease or disorder, the overall health status of the particular patient, the relative biological efficacy of the compound selected, and formulation of the compound excipient, and its route of administration.

The daily dose of the H3 antagonist/inverse agonist (I) may generally be comprised between 1 µg and 50 mg a day per patient. As an illustration, the preferred doses for pitolisant are 5-40 mg/day, more preferably 10-30 mg/day, and for BP1.3656B 1-100 µg/day, preferably 5-30 µg/day The daily dose of the antidepressant may generally be comprised between 2 mg and 250 mg a day per patient. Illustrated doses are detailed below:
Desipramine: 10-300 mg/day, preferably 25-200 mg/day;
Duloxetine: 20-120 mg/day, preferably 30-60 mg/day; Venlafaxine: 35-375 mg/day, preferably 35-225 mg/day; Desvenlafaxine: 50-400 mg/day, preferably 50-100 mg/day; Atomoxetine: 10-100 mg/day, preferably 10-60 mg/day; Reboxetine: 2-12 mg/day, preferably 2-8 mg/day.

According to a further embodiment, the method of the invention also comprises the administration of one or more further active ingredient, selected from anti-Parkinson drugs such as levodopa, ropinirole, lisuride, bromocriptine, pramixepole or selected from anti-narcoleptic or purported anti-narcoleptic drugs from another class including modafinil.

The compounds can be formulated into the same or distinct pharmaceutical compositions by admixture with one or more pharmaceutically acceptable excipients.

The compositions may conveniently be administered in unit dosage form and may be prepared by any of the methods well known in the pharmaceutical art, for example, as described in *Remington: The Science and Practice of Pharmacy*, 20$^{th}$ ed.; Gennaro, A. R., Ed.; Lippincott Williams & Wilkins: Philadelphia, PA, 2000.

The compounds may be administered by various administration routes such as oral; parenteral including sub-cutaneous, intramuscular, intra-venous; sublingual, topical; local; intratracheal; intranasal; transdermal or rectal, the active ingredients being combined with a pharmaceutically acceptable excipient or vehicle in one or two pharmaceutical compositions.

In particular, the formulations suitable for parenteral administration are sterile and include emulsions, suspensions, aqueous and non-aqueous injection solutions, which may contain suspending agents and thickening agents and anti-oxidants, buffers, bacteriostats and solutes which render the formulation isotonic, and have a suitably adjusted pH, with the blood of the intended recipient. For the topical application, the compositions of the invention may be used as creams, gels, ointments or lotions.

According to the invention, oral administration of the compound (I) or composition in an appropriate formulation is advantageously used. Formulations which are suitable to be administered orally to a patient include discrete units such as capsules, such as soft or hard gelatine, tablets, each containing a predetermined amount of the compound of formula (I). They also include powder; granules; solutions or suspensions in an aqueous liquid or a non-aqueous liquid, or oil-in-water liquid emulsion or water-in-oil liquid emulsion. Gastrointestinal resistant formulations are also contemplated for oral formulations, in particular for duloxetine.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable excipient, vehicle or carrier" includes in particular diluents, adjuvants, excipients, or vehicles. The use of such ingredients for pharmaceutical active substances is well known in the art.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/medicament according to the present invention effective in producing the desired therapeutic effect.

According to the invention, the term "patient", or "patient in need thereof", is intended for a human or non-human mammal affected or likely to be affected with the above disorders. Preferably, the patient is a human.

The compounds may be administered in unit dosage forms, wherein the term "unit dose" means a single dose which is capable of being administered to a patient, and which can be readily handled and packaged, remaining as a physically and chemically stable unit dose comprising either the active compound itself, or as one or two pharmaceutically acceptable compositions.

The appropriate unitary dosage forms comprise the oral forms; the sublingual, buccal, intratracheal, intraocular, intranasal forms, by inhalation, the topical, transdermal, sub-cutaneous, intramuscular or intra-venous, and the rectal forms and the implants.

BRIEF DESCRIPTION OF THE DRAWINGS

The invention will be described in connection with the attached drawings, in which.

DESCRIPTION OF THE PREFERRED EMBODIMENTS

Examples

Example 1: Effect on Sleep/Wake

Effects on sleep/wake parameters were investigated in male Wistar rats. Briefly, rats were stereotaxically implanted with cortical electrodes for electroencephalogram (EEG) recording using a telemetric system (Data Sciences Int., Saint Paul, MN, USA) for the acquisition, transfer and storage of motor activity and EEG signals. EEG signals were analysed according to a procedure adapted from the algorithm proposed by R. P. Louis et al. (J. Neurosci. Methods, 2004, 133, 71-80) and the analysis of vigilance stages according to H. Kleinlogel (Neuropsychobiol. 1990-91, 23, 197-204) after a fast Fourier transformation of 8-second duration EEG epochs. This allows the determination for each epoch of its vigilance stage (i.e. active wakefulness, quiet wakefulness, light or deep slow wave sleeps and REM sleep also named paradoxical sleep). Rats received orally (gavage) vehicle, drug or drug combination around 30 minutes before the light onset. Then, EEG signals were continuously recorded and further integrated over the 12-hour diurnal phase.

Figure 1:
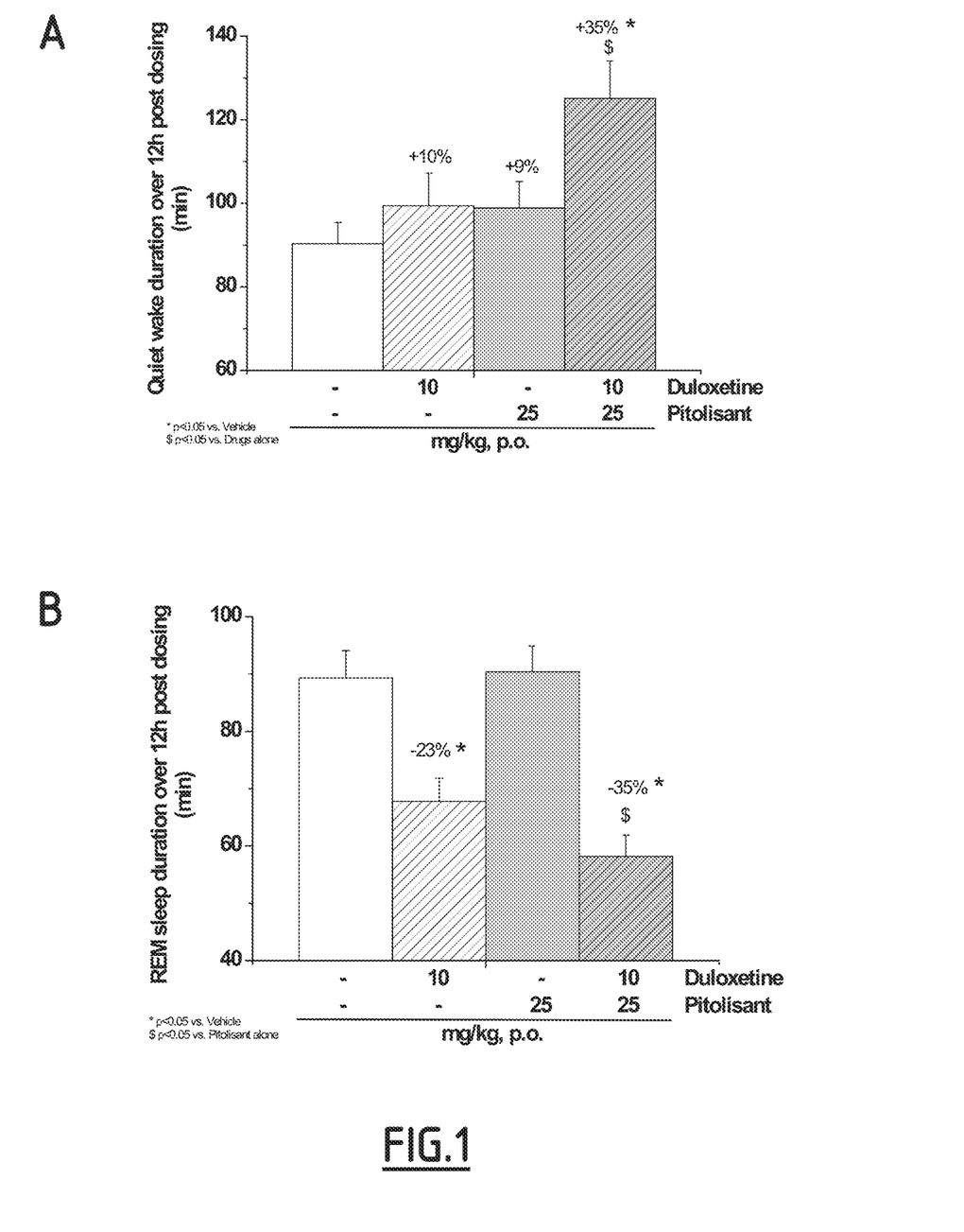
FIG. 1 represents the drug-induced changes in sleep-wake balance over 12 hours post dosing in rats (Mean±SEM of 15 to 16 individual values) in quiet wake duration (FIG. 1A) and REM sleep duration (FIG. 1B) following administration of pitolisant and duloxetine.
Figure 2:
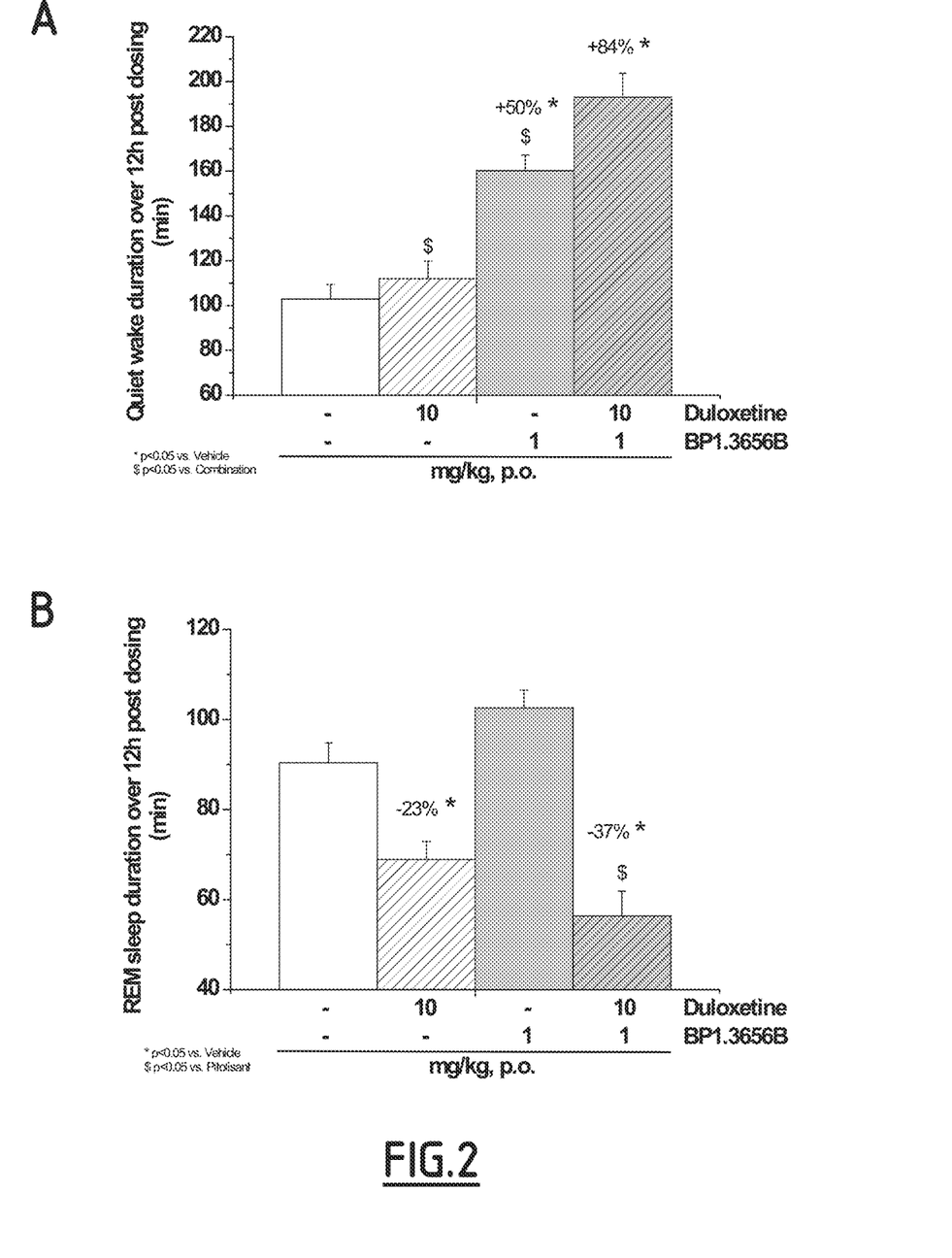
FIG. 2 represents the drug-induced changes in sleep-wake balance over 12 hours post dosing in rats (Mean±SEM of 15 to 16 individual values) in quiet wake duration (FIG. 2A) and REM sleep duration (FIG. 2B) following administration of compound BP1.3656B and duloxetine.
Figure 3:
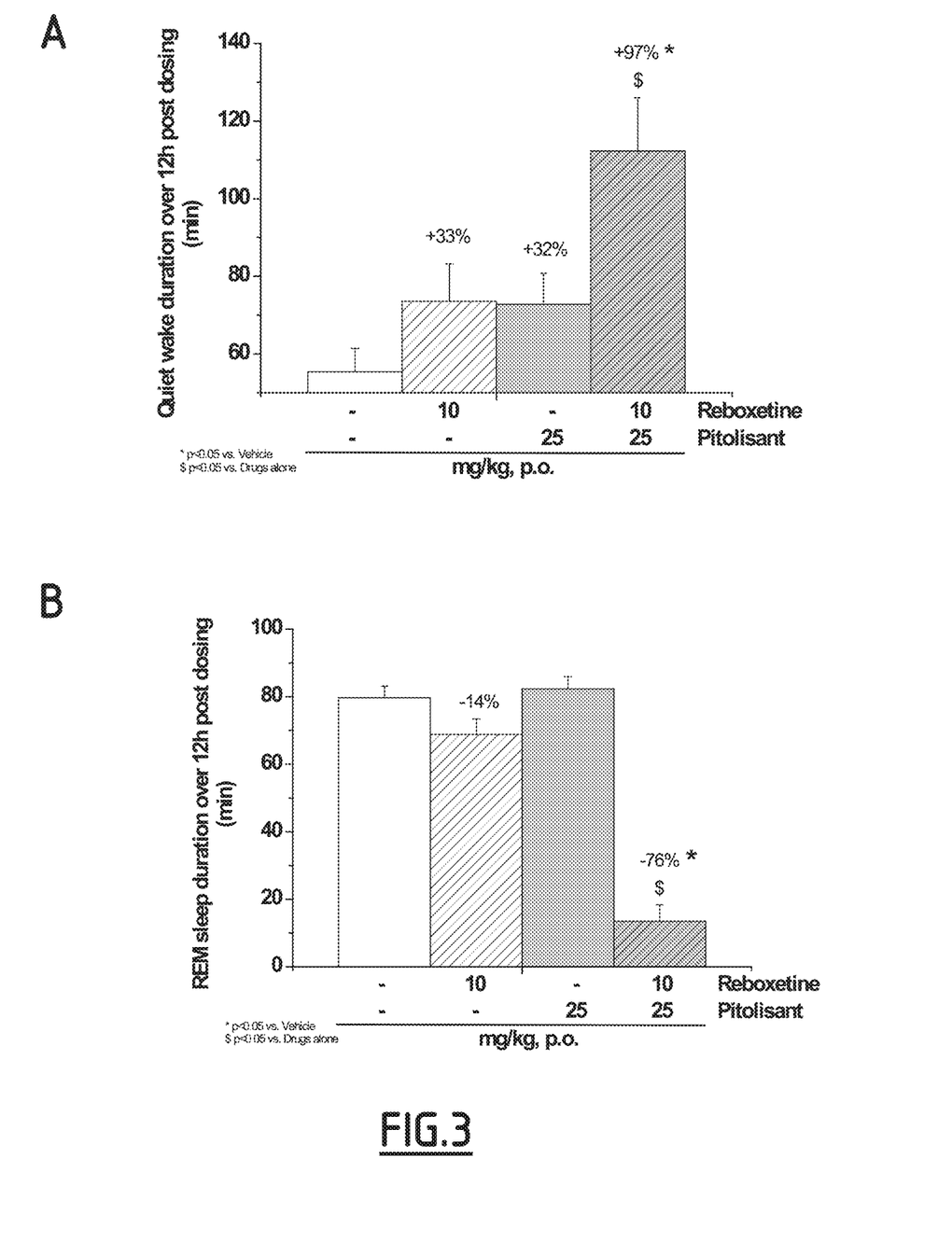
FIG. 3 represents the drug-induced changes in sleep-wake balance over 12 hours post dosing in rats (Mean±SEM of 15 to 16 individual values) in quiet wake duration (FIG. 3A) and REM sleep duration (FIG. 3B) following administration of pitolisant and reboxetine.
Figure 4:
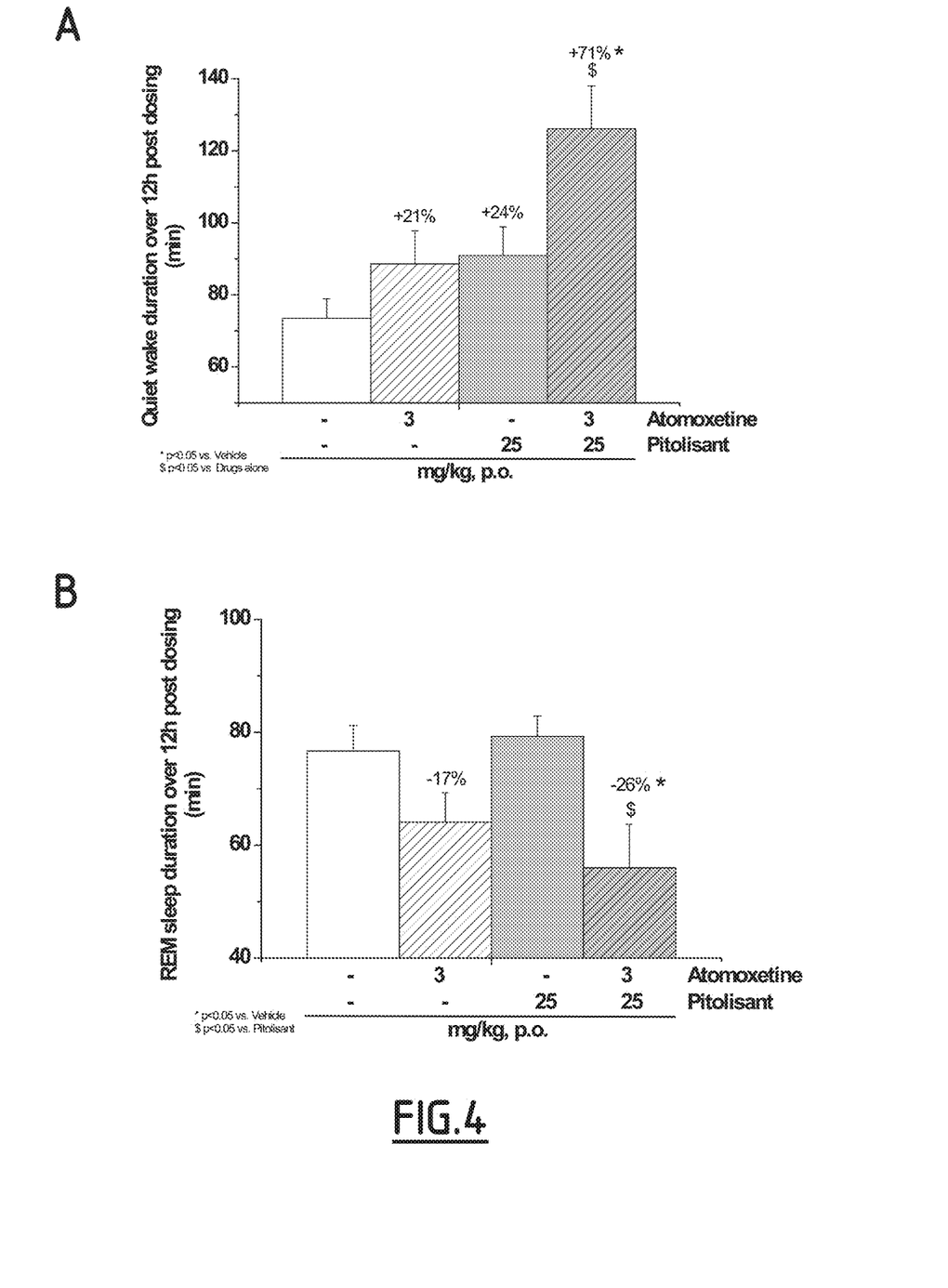
FIG. 4 represents the drug-induced changes in sleep-wake balance over 12 hours post dosing in rats (Mean±SEM of 15 to 16 individual values) in quiet wake duration (FIG. 4A) and REM sleep duration (FIG. 4B) following administration of pitolisant and atomoxetine.

Effects on sleep/wake recorded in rats of drugs alone or combined are presented in the FIG. 1 (Pitolisant/duloxetine), FIG. 2 (BP1.3656B/duloxetine), FIG. 3 (pitolisant/reboxetine) and FIG. 4 (pitolisant/atomoxetine):

In the case of the pitolisant/duloxetine combination, the combination was shown to lead to an increase in the quite wake of +35% as compared to a cumulated increase of +19%. In addition, when the two compounds are combined, the decrease in the REM sleep elicited by duloxetine is potentiated compared to the effect of duloxetine alone (−35% vs. −23%) whereas pitolisant itself over 12 hours does not have any significant effect.

Example 2: Noradrenaline Release in the Prefrontal Cortex

Both histamine H3 receptor antagonist/inverse agonists (J. S. Lin et al. Neurobiology of Disease 2008, 30, 74, G. Flik et al. J. Mol. Neurosci. 2015, 56, 320) and noradrenaline reuptake inhibitors (F. P. Bymaster et al. Current Pharmaceutical Design, 2005, 11, 1475, F. P. Bymaster et al. Neuropsychopharmacol. 2002, 27, 699) are known to enhance the extracellular noradrenaline in the prefrontal cortex and reflecting an activation of the noradrenergic neurotransmission. However, in both cases, the enhancement is limited.

Effects on noradrenaline release in the prefrontal cortex were investigated in vivo by microdialysis in vigil male Wistar rats as described by AD Medhurst et al. (J. Pharmacol. Exp. Ther. 2007, 321, 1032-1045) and G. Flik et al. (J. Mol. Neurosci. 2015, 56, 320-328). Briefly, anaesthetized rats were implanted with a guide cannulae for sampling in the prefrontal cortex. After at least one week of recovery post-surgery, the microdialysis probe was inserted in the guide cannulae and perfused continuously with artificial cerebrospinal fluid (CSF). The rat was habituated to the microdialysis cage for ~3 hours. Then, rats received orally (gavage) vehicle, drug or drug combination. CSF samples collected every 30 minutes were analysed for their noradrenaline content by HPLC coupled to a electrochemical detection. Noradrenaline sample levels were expressed in percentage of basal noradrenaline release recorded over 1.5 hour before vehicle or drug treatment.

Figure 5:
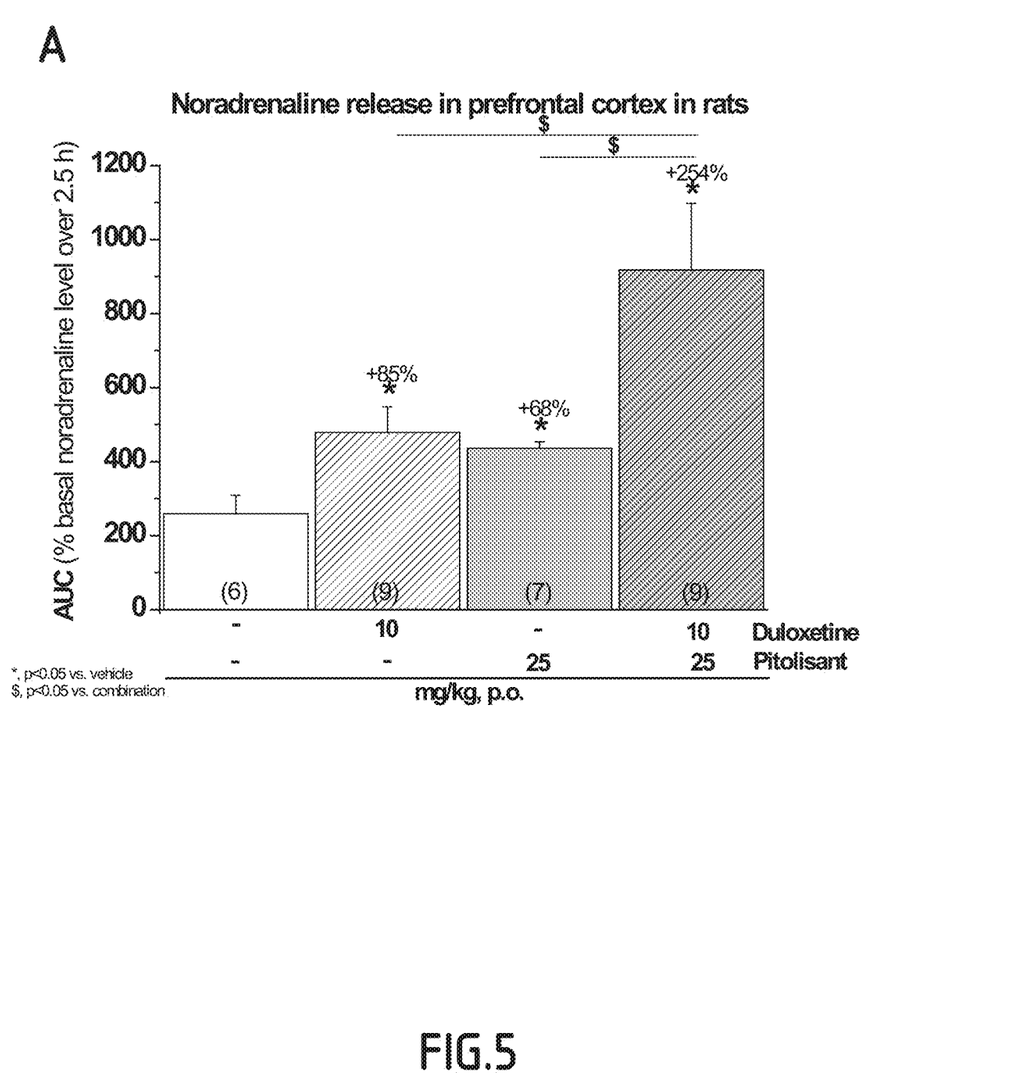
FIG. 5 represents the drug-induced increase in noradrenaline release in rat prefrontal cortex over basal release (AUC over 150 min post dosing) following administration of pitolisant and duloxetine (Mean±SEM of 6 to 9 individual values).

Unexpectedly, when the two types of compounds are combined, the activation of the noradrenergic neurotransmission in the prefrontal cortex is enhanced in a synergistic manner as shown by the following data and illustrated in FIG. 5:

| | Maximal increase recorded over 150 min post dosing | | | |
|---|---|---|---|---|
| drug | Maximal increase (% of basal noradrenaline release) | statistics p value versus | | |
| | | saline | pitolisant | duloxetine |
| pitolisant | +148 ± 49% | >0.05 | | |
| duloxetine | +113 ± 31% | <0.05 | | |
| combination | +385 ± 115% | <0.05 | <0.05 | <0.05 |

Hence, the association of the two classes of compounds may allow a decrease in the dosage of each component and, thereby, enhanced tolerance.

The invention claimed is:

1. A method for treating excessive daytime sleepiness in a patient suffering from deficient noradrenaline release, comprising administering to a patient in need thereof a combination of pitolisant or a pharmaceutically acceptable salt thereof and an antidepressant chosen from the noradrenaline reuptake inhibitors duloxetine, reboxetine and atomoxetine, wherein said pitolisant and said antidepressant are administered in relative amounts such that said combination following administration to the patient displays a synergistic effect as to at least one of (a) an increase of quiet wake duration, and (b) a decrease in REM sleep duration.

2. The method according to claim 1, wherein said pitolisant or a pharmaceutically acceptable salt thereof is the hydrochloride salt of pitolisant.

3. The method according to claim 1 comprising the administration of of or a pharmaceutically acceptable salt thereof, with duloxetine.

4. The method according to claim 1, wherein both ingredients are administered simultaneously, separately, or staggered over time.

5. The method according to claim 1, wherein said disorder is excessive daytime sleepiness and occurs in a patient suffering from:
- Narcolepsy with and without cataplexy,
- Idiopathic hypersomnia,
- Daytime sleepiness disorders,
- Obstructive sleep apnea,
- Circadian rhythm sleep-wake disorders,
- Parkinson's disease, or
- Prader-Willi Syndrome.

* * * * *